(12) United States Patent
Sardo

(10) Patent No.: US 10,531,671 B2
(45) Date of Patent: Jan. 14, 2020

(54) ANTI-SPROUTING COMPOSITIONS FOR COATING BULBS AND TUBERS AND THE USE THEREOF FOR ANTI-SPROUTING TREATMENT

(71) Applicant: XEDA INTERNATIONAL S.A., Saint Andiol (FR)

(72) Inventor: Alberto Sardo, Chateaurenard (FR)

(73) Assignee: XEDA INTERNATIONAL S.A., Saint Andiol (FR)

( * ) Notice: Subject to any disclaimer, the term of this patent is extended or adjusted under 35 U.S.C. 154(b) by 113 days.

(21) Appl. No.: 15/111,487

(22) PCT Filed: Jan. 20, 2015

(86) PCT No.: PCT/EP2015/050928
§ 371 (c)(1),
(2) Date: Jul. 14, 2016

(87) PCT Pub. No.: WO2015/107206
PCT Pub. Date: Jul. 23, 2015

(65) Prior Publication Data
US 2016/0330987 A1 Nov. 17, 2016

(30) Foreign Application Priority Data

Jan. 20, 2014 (FR) .................................. 14 50435
Jun. 13, 2014 (FR) .................................. 14 55442

(51) Int. Cl.
*A23B 7/16* (2006.01)
*A01N 3/00* (2006.01)

(52) U.S. Cl.
CPC .................. *A23B 7/16* (2013.01); *A01N 3/00* (2013.01); *A23V 2002/00* (2013.01)

(58) Field of Classification Search
CPC .......... A01N 25/02; A01N 25/04; A23B 7/16; A23V 2002/00
USPC .......... 426/310, 93, 102, 615, 637, 601, 654
See application file for complete search history.

(56) References Cited

U.S. PATENT DOCUMENTS

| 3,533,810 A * | 10/1970 | Shillington |
| 4,123,558 A | 10/1978 | Poapst et al. |
| 2002/0032171 A1 | 3/2002 | Chen et al. |
| 2009/0274772 A1* | 5/2009 | Bowker et al. |
| 2011/0251167 A1 | 10/2011 | Dudley et al. |
| 2012/0251675 A1* | 10/2012 | Sowa et al. |

FOREIGN PATENT DOCUMENTS

| EP | 2 225 940 A1 | 9/2010 |
| FR | 2 563 974 A1 | 11/1985 |
| FR | 2 891 438 A1 | 4/2007 |

(Continued)

OTHER PUBLICATIONS

Abstract, of MT Wu et al., "A Research Note: Use of Spray Lecithin for Control of Greening and Glycoalkaloid Formation of Potato Tubers," Journal of Food Science, Sep. 1977.

(Continued)

*Primary Examiner* — Helen F Heggestad
(74) *Attorney, Agent, or Firm* — Eric L. Lane; Green Patent Law

(57) ABSTRACT

The present invention relates to novel compositions and their use for anti-sprouting treatment of potatoes.

20 Claims, 1 Drawing Sheet

(56) References Cited

FOREIGN PATENT DOCUMENTS

| GB | 2 419 888 A | 5/2006 |
|----|----|----|
| WO | WO 01/01960 A1 | 1/2001 |
| WO | WO 2006/113505 A2 | 10/2006 |
| WO | WO 2007/060174 A1 | 5/2007 |
| WO | WO 2009/068802 A1 | 6/2009 |
| WO | WO 2010/091871 A1 | 8/2010 |
| WO | WO 2011/095751 A1 | 8/2011 |

OTHER PUBLICATIONS

Preliminary Search Report dated Jun. 25, 2014 in priority application No. FR 1450435.
International Search Report dated Mar. 18, 2015 in related International Application No. PCT/EP2015/050928.

* cited by examiner

ANTI-SPROUTING COMPOSITIONS FOR COATING BULBS AND TUBERS AND THE USE THEREOF FOR ANTI-SPROUTING TREATMENT

The present invention relates to novel compositions for the coating of bulbs and tubers, as well as an anti-sprouting treatment method for applying the compositions to the bulbs and tubers.

Sprouting is a critical issue in the conservation of potatoes and coating compositions generally based on synthetic active agents such as CIPC have been proposed. One also seeks to avoid the phenomenon of the respiration of potatoes which results in weight loss and a withered appearance that is off-putting for consumers.

Coating compositions to prevent the greening and sprouting of potatoes based on acceptable ingredients in food are known. Thus, Wu et al (J. Amer. Soc. Hort. Sci. 97(5) 614-616, 1972) proposed corn oil-based compositions. Nevertheless, the resulting oily coatings create a phenomenon of condensation with ambient humidity.

U.S. Pat. No. 2,755,189 describes compositions based on wax. However, the film thus formed requires drying and the coating is effected by immersion in a hot wax that can damage the potatoes.

WO 2010/031983 describes the application of coating compositions on bulbs or tubers. However, these compositions are based on resins and require drying of the potatoes before and after treatment. This implies additional facilities and significant additional cost.

It is therefore desirable to make available a new coating process to fight against the sprouting and/or weight loss of the bulbs and tubers.

Thus, the invention is more particularly targeted at coating compositions that are acceptable for foodstuffs for bulbs and tubers, enabling the effective prevention or delay of sprouting and according to a method that is easy to implement.

According to a first object, the present invention therefore relates to an anti-sprouting composition for bulbs and tubers comprising:
  one or more lipophilic components selected from among vegetable oils, mineral oils, lecithin, fatty acids and mixtures thereof,
  an emulsifier or mixture of emulsifiers selected from among anionic or nonionic emulsifiers with a high hydrophilic/lipophilic balance (HLB),
  a solvent selected from among water, monopropylene glycol, ethanol and mixtures thereof.

With respect to bulbs and tubers, the present invention is aimed particularly at potatoes.

According to one embodiment, the said composition is in the form of an aqueous solution or aqueous dispersion.

According to one embodiment, the said composition comprises monopropylene glycol.

Typically, the said composition comprises from 5 to 50%, especially 10 to 40% of the said oily component in water.

By non-ionic emulsifiers with a high hydrophilic/lipophilic balance (HLB) are meant emulsifiers with an HLB between 8 and 14, in particular above 6.

Among nonionic emulsifiers with a high hydrophilic/lipophilic balance (HLB) may be mentioned ethoxylated fatty acids such as oleic acid ethoxylate 10 moles, sugar esters, sugar glycerides, polyalkylglucosides, polyalkylglucoside esters, tweens, ethoxylated fatty alcohols such as ethoxylated lauryl alcohol 6, 10 or 12 moles, fatty acid salts and mixtures thereof.

The term "vegetable oil" means any vegetable oil consisting of glycerin triesterified by fatty acids, in particular such as oleic acid. One may mention sunflower, soybean, rapeseed, corn, peanut and olive oils.

Thus, although the compositions described above have an anti-sprouting effect, it is possible to add one or more anti-sprouting agents.

According to one embodiment, the compositions may also further comprise one or more other agents, such as fungicides, bactericides and/or antioxidants, particularly one or more antioxidants.

The essential oils are known to have such effects.

Thus, in one embodiment, the compositions according to the invention may further comprise one or more essential oils. Generally speaking, the said compositions comprise from 2 to 10 wt.-% of essential oil.

The term "essential oil" as used here refers to the essential oil as well as one of its constituents and/or mixtures thereof. The term "constituent" as used here refers to the active ingredients, i.e. those having an anti-sprouting, bactericidal, fungicidal and/or antioxidant effect.

Thus, among essential oils may in particular be mentioned mint oil and/or thyme oil and/or oregano oil and/or clove oil, and their constituents, i.e. L-carvone, thymol, carvacrol and respectively and/or mixtures thereof eugenol; more particularly peppermint oil, clove oil, L-carvone and eugenol.

The said oils generally comprise from 50 to 90% of the said constituent; thus, clove oil generally contains about 80% of eugenol and peppermint oil about 70% of L-carvone.

Among antioxidants may also be mentioned citric acid, tartaric acid, acetic acid, ascorbic acid and mixtures thereof, and salts thereof.

Thus, one embodiment of the composition according to the invention may optionally comprise eugenol, citric acid, ascorbic acid, tartaric acid and/or acetic acid, as well as the salts of these acids.

It is to be understood that citric acid, tartaric acid, ascorbic acid or acetic acid may be present in their free form (acid) or in their salt form associated with a cationic ion-cons.

As for salt, mention may be made of alkali metal salts, such as potassium, sodium salts.

According to one embodiment, the composition comprises:
  from 0.1 to 20%, especially 1 to 10% of the said oily component(s), and/or
  from 10 to 80%, especially 20 to 70% of solvent(s); and/or
  from 1 to 30%, especially 10 to 20% of emulsifier(s), and/or
  from 0 to 10%, especially 1 to 8% of antioxidant(s).

According to one embodiment, the composition comprises:
  from 0.1 to 20% of the said oily component(s);
  from 10 to 80% of solvent(s);
  from 1 to 30% of emulsifier(s), and
  from 0 to 10% of anti-oxidant(s).

According to one embodiment, the composition comprises:
  from 0.1 to 10% of lecithin;
  from 10 to 80% of solvent comprising monopropylene glycol and water;
  from 1 to 30% of emulsifier(s) selected from ethoxylated oleic acid, lauric alcohol, sucrose esters, and mixtures thereof; and
  from 0.1 to 10% of citric acid or alkali citrate.

According to one embodiment, the compositions of the invention are free of resin or wax.

According to another embodiment, the compositions of the invention may comprise one or more additives, particularly known for the phytosanitary effect they provide.

The compositions according to the invention also offer the advantage of reducing the phytotoxicity which may be observed upon application of essential oils and/or their constituents. Thus, the compositions according to the invention exhibit less phytotoxicity than concentrated formulations with a total equivalent dose of active ingredient.

On the other hand, solutions according to the invention are perfectly stable up to several months, preferably at least one month, at low temperature, preferably up to 0° C. This allows the end user to store the compositions in cold rooms, for example.

According to another object, the present invention also relates to a bulb or tuber coated with a film consisting of a composition according to the invention.

According to another object, the present invention also relates to the method for preparing the said compositions.

The said method comprises mixing the constituents, for example through stirring.

According to one embodiment, the compositions are prepared by mixing the emulsifier and ethanol and possibly solvent, in vegetable oil, preferably at room temperature, and then adding any essential oil while stirring.

If necessary, it is possible to heat the reaction mixture to obtain a satisfactory dissolution.

If necessary, the resulting compositions are left to stand for a period between a few hours and several days before use.

The composition provides a strengthened anti-sprouting effect, so that it is possible to use very low application rates. Thus, the coating process is said to be ULV (Ultra Low Volume).

According to another of its objects, the present invention also relates to a method for anti-sprouting treatment of bulbs and tubers comprising applying from 0.1 to 2 kg of the composition according to the invention per tonne of bulbs and tubers.

Advantageously, the method comprises applying 0.2 to 1 kg of composition per tonne of bulbs and tubers.

The optimal amount of treatment composition to be applied to bulbs and tubers depends on the nature of the bulbs and tubers concerned and the selected application method.

Unexpectedly and advantageously, the compositions according to the invention do not require drying of the bulbs and tubers prior to coating.

According to one embodiment, the method according to the invention comprises applying the said composition to wet bulbs or tubers.

Advantageously, it is not necessary to dry the bulbs and tubers to be coated by the said composition.

According to one embodiment, the method therefore does not include a drying step, previous and/or subsequent to the coating.

According to one embodiment, the said method comprises applying the said composition by means of the device described in the application WO 2010/031983 that is incorporated herein by reference.

More specifically, the method according to the invention may include applying the composition by means of a bulb or tuber coating device, wherein the device has a coating zone comprising:
 a coating conveyor for conveying the bulbs or tubers in a longitudinal direction;
 a device for applying a coating composition on the bulbs or tubers conveyed on the coating conveyor;
 characterized in that the coating conveyor comprises a frame, a plurality of rotating brushes fixed in the longitudinal direction with respect to the frame, and a motor assembly to rotate the brushes about their respective axes transverse to the chassis, wherein the brushes are arranged in order to define together a surface for the supporting and conveying of the bulbs or tubers, and wherein the bulbs or tubers are rolled over during application of the coating composition.

According to one embodiment, the application device projects the coating composition on the bulbs or tubers at a controlled pressure greater than atmospheric pressure.

The application device comprises at least one projection member arranged above the coating conveyor, and a metering member to supply the projection member with coating composition at a controlled rate.

The brushes generally have an outer diameter between 60 and 180 mm.

Other characteristics and advantages will emerge from the description of the system below.

The device comprises:
 a bulb or tuber coating zone;
 a coated bulb or tuber drying zone;
 a closed enclosure in which is disposed the coating zone.

The coating zone comprises a coating conveyor provided to convey the food products in a longitudinal direction, and a device for applying a coating composition on the bulbs or tubers conveyed on the conveyor.

The coating zone comprises a conveyor frame, a plurality of rotating brushes mounted on the chassis, and a motor assembly to rotate the brushes about respective axes transverse to the chassis.

The brushes are cylindrical and each have an outer diameter between 60 and 180 mm, preferably between 80 and 120 mm. In any event, the brushes should have an outer diameter greater than the diameter of the bulbs or tubers to be treated.

The brushes are fixed in translation according to the longitudinal and transverse directions relative to the frame. They therefore represent only one degree of freedom relative to the frame when rotating about their respective axes.

The brushes are arranged parallel to each other, and are evenly spaced longitudinally. The spacing is provided so that the brushes are substantially at a tangent to each other, or so that the bristles of each brush penetrate slightly into those of the neighboring brushes. The axes of the brushes are located in a same substantially horizontal plane, so that the brushes together define a supporting and conveying surface for the bulbs or tubers. Thus, the bulbs or tubers deposited at an upstream end of the surface are driven by the brushes towards the downstream end of the surface. Brushes are provided to roll the bulbs or tubers over during the longitudinal movement of these products from the upstream end towards the downstream end of the surface, regardless of their size and shape, even in the case of flat potatoes.

This rolling is first obtained by the fact that the surface has bumps, at the tops of the brushes and in the troughs between the brushes. The bulb or tuber reaching the top of a bump will roll into the next trough. Furthermore, the brush bristles, by pressing against the outer surface of the bulb or tuber, tend to turn this in the opposite direction to the brush. This movement is similar to the driving of a gear by a pinion.

The motor drive assembly rotates the brushes about their respective axes. The brushes are all designed to rotate in the same direction.

The coating composition application device is designed to project the coating composition on the bulbs or tubers being conveyed on the coating conveyor at a controlled pressure greater than atmospheric pressure, and at a controlled rate. The pressure and flow rate are selected according to the type of bulb or tuber to be treated, and as a function of the nature of the coating composition.

The application device typically comprises a tank for storing a supply of coating composition, a plurality of nozzles distributed longitudinally above the conveyor, and a metering member to supply the nozzles with coating composition from the tank.

The sprinkler may be of any suitable type. It typically includes a nozzle for adjusting the width of the coating composition jet projected towards the conveyor. The metering member is, for example, a metering pump with an adjustable flow.

The sprinkler projection nozzles are typically placed 15 cm above the surface on which the bulbs or tubers are conveyed.

The coating composition flow rate is typically between 1 and 10 liters per tonne and preferably 2 to 5 liters per hour. The supply pressure of the nozzles is typically between 1 and 10 bar, preferably 2 to 5 bar.

Although the device according to the invention is not limited as to the nature of the applied coating compositions, it is particularly suitable for the application of coating compositions according to the invention.

The operation of the coating device described above will now be detailed.

The bulbs or tubers to be coated are deposited at the upstream end of the conveyor surface of the coating. They are deposited manually by an operator, or are fed from another conveyor.

The bulbs or tubers are conveyed longitudinally from the upstream end to the downstream end by the brushes. The hairs of the brushes slide against the skin of the bulbs or tubers causing these products to be conveyed longitudinally.

The bulbs or tubers generally have rounded forms, for example apples, pears, citrus fruits, potatoes, etc., and roll during their longitudinal conveyance on the coating conveyor.

During the conveyance of the bulbs or tubers on the conveyor, the application device projects the coating composition on the bulbs or tubers. The pump sucks the coating solution in the reservoir and supplies the composition to the nozzles at a given pressure and at a given flow rate. The sprinklers project the coating composition downwards, i.e. towards the bulbs or tubers. Because the bulbs or tubers are rolling on the conveyor surface, all the areas of the skin of the bulbs or tubers successively face the sprinkler and receive a dose of the coating composition. Thus, the fact that the bulbs or tubers roll on the conveyor and an application device is used to project the coating composition on the bulbs or tubers at a controlled rate and at a controlled pressure, allows excellent control of the thickness of the coating composition deposited on the surface of the bulb or tuber, resulting in a particularly uniform application over the entire skin of the bulb or tuber.

The bulbs or tubers leave the coating conveyor at the downstream end of the surface and move directly to an end station where they are taken off by hand by operators in order to be packaged or, for example, transferred to another conveyor.

Thus, the coating device described above allows a coating of good quality to be obtained for all kinds of bulbs or tubers.

The fact that the coating conveyor comprises brushes to roll over the bulbs or tubers during application of the coating composition contributes to obtaining a film of uniform and controlled thickness of a coating composition on the bulbs or tubers.

The coating device may be in the form of many variants. The number of coating conveyor rollers may vary as a function of the needs. The number of nozzles may also vary; only one nozzle or a large number of nozzles may be provided depending on the type and size of the bulbs or tubers to be treated, the speed of conveyance of the bulbs or tubers on the surface of the coating conveyor, the type of coating composition, etc.

The application device should not be of the type designed to project the coating composition under a pressure greater than atmospheric pressure. The application device could be a showering device, provided to spray the coating composition on the bulbs or tubers at a pressure corresponding to atmospheric pressure. The application device may also be a device for spraying by nebulization or atomization.

Advantageously, drying of the composition is carried out by simple contact of the coated bulbs and tubers with ambient air. It is not necessary to provide further drying means such as a drying conveyor, an air inlet and outlet, an air circulation unit.

Thus, in one embodiment, the coating device does not have a drying conveyor, an air inlet and outlet, and/or an air circulation unit.

According to one embodiment, the method according to the invention includes the preliminary step of cleaning the said bulbs or tubers, for example, by washing, optionally followed by drying, or by dry brushing.

According to one embodiment, the method may comprise a step to preheat the composition in order to reduce the viscosity and improve the quality of the coating.

The application may be carried out once or several times during storage.

The composition according to the invention primarily has an anti-sprouting effect. It seems that this effect is related to the fine homogenous layer created by the method according to the invention which allows neutralization of the gaseous exchanges between the potato and the surrounding air. Thus, the anti-sprouting effect of the compositions according to the invention may be accompanied by an anti-sweating effect.

By an "anti-sprouting and/or anti-sweating" effect according to the invention is meant an effect that inhibits and/or delays the sprouting and/or weight loss.

According to another object, the present invention also relates to a method of treatment to prevent or delay the sprouting and/or the weight loss of the bulbs and tubers, through the implementation of the coating process according to the invention.

Of course, the preferred embodiments indicated above or below may be implemented singly or in combination.

Unless otherwise stated, the percentages given above and below are by weight/volume.

The invention is illustrated by the examples and FIGS. 1 and 2 below.

Figure 1:
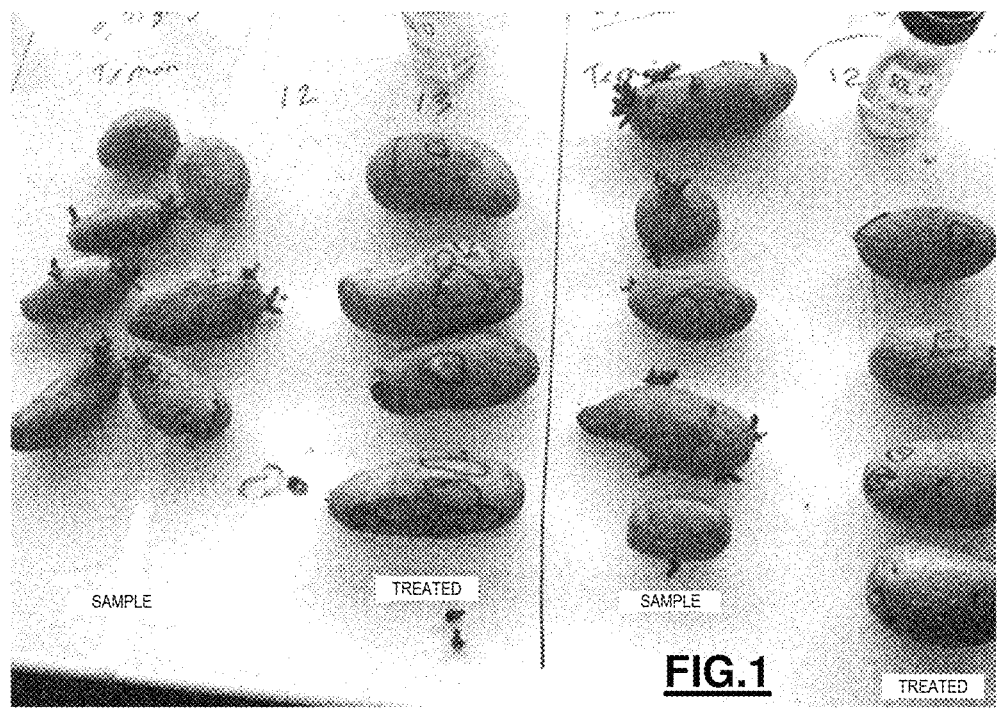
FIG. 1 illustrates the effect of the compositions according to the invention on sprouting compared to reference compositions under the conditions of example 3.
Figure 2:
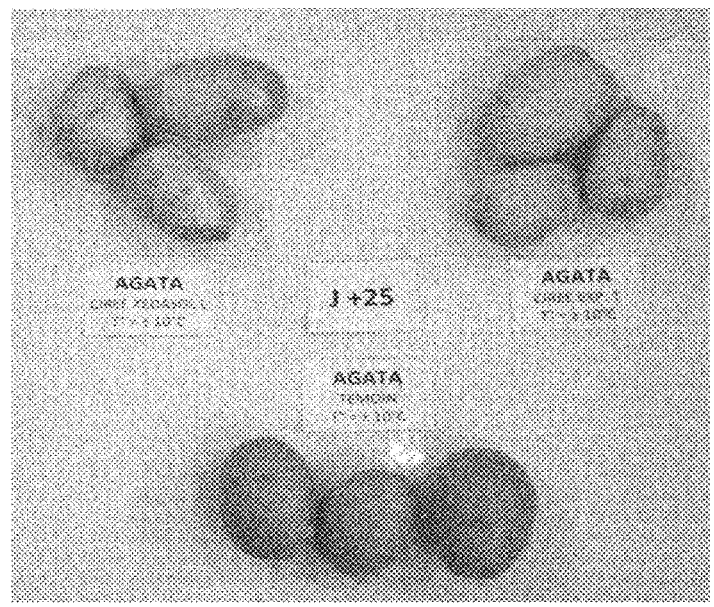
FIG. 2 illustrates the effect of compositions applied according to the invention on the sprouting of potatoes compared with reference compositions and conditions of application described in WO 2010/031983, as described in example 4.

The following examples are illustrative and not limiting on the present invention.

EXAMPLE 1 PREPARATION OF A COMPOSITION ACCORDING TO THE INVENTION

The following are mixed while stirring:
10% lecithin;
35% monopropylene glycol;
31% water;
10% ethoxylated oleic acid 10 moles;
5% lauric alcohol 10 moles;
3% of sucrose esters;
6% potassium citrate.
in order to obtain a stable and clear solution.

EXAMPLE 2 APPLICATION

The composition of example 1 is applied to potatoes being storage by ULV spray at a rate of 0.75 g/kg of potatoes.

EXAMPLE 3 DETERMINATION OF ANTI-SPROUTING EFFECT

This study was effected to evaluate the efficacy of the composition of example 1 in inhibiting the sprouting of potatoes.

The Chérie variety was used for this test and as a comparison.

One treatment was performed for batches 1 and 2 below:

Batch 1: the treated and comparison potatoes were stored for 30 days after treatment at room temperature, in daylight without special protection.

Batch 2: the treated and comparison potatoes were stored for 40 days after treatment at room temperature, in daylight without special protection.

For each batch, the treated and comparison potatoes were compared visually. FIG. 1 illustrates the results obtained. It appears that sprouting is substantially inhibited in the treated potatoes.

EXAMPLE 4 DETERMINATION OF THE ANTI-SPROUTING EFFECT COMPARED TO A RESIN COMPOSITION

The Agata variety of potatoes was treated respectively by the composition of example 1 applied according to example 2 (batch "waxed exp.1") and a shellac-based resin composition described and applied according to WO 2010/031983 (batch "waxed xedasol I"). The potatoes were stored at 10° C. for 25 days after treatment.

The results are shown in FIG. 2. The formation of nuclei is inhibited on the groups treated according to the invention. There is also an inhibition of greening for these treated groups.

The invention claimed is:

1. Anti-sprouting composition for application on wet bulbs and tubers consisting of:

0.1 to 20% (weight/volume) of, 1 to 30% (weight/volume) of an emulsifier or mixture of emulsifiers selected from among anionic or non-ionic emulsifiers with a high hydrophilic/lipophilic balance (HLB), 10 to 80% (weight/volume) of a solvent selected from among water, monopropylene glycol, ethanol and mixtures thereof, wherein the composition comprises one or more antioxidants selected from citric acid, clove oil, and eugenol, and wherein the composition coats the wet bulbs and tubers.

2. Composition according to claim 1 wherein said composition is in the form of an aqueous solution or aqueous dispersion.

3. Composition according to claim 1 wherein said composition comprises monopropylene glycol.

4. Composition according to claim 1, wherein the nonionic emulsifiers with a high hydrophilic/lipophilic balance (HLB) are selected from among ethoxylated fatty acids, sugar esters, sugar glycerides, polyalkylglucosides, tweens, polyalkylglucoside esters, ethoxylated fatty alcohols, fatty acid salts, and mixtures thereof.

5. The composition according to claim 4, wherein the ethoxylated fatty alcohols are chosen from ethoxylated lauryl alcohol 6, 10 or 12 moles.

6. Composition according to claim 1 wherein said composition comprises from 0 to 10% of anti-oxidant(s).

7. Bulb or tuber coated with a film consisting of a composition according to claim 1.

8. Method of anti-sprouting treatment of bulbs and tubers, comprising the application of 0.1 to 2 kg of composition according to claim 1 per tonne of tubers and bulbs.

9. Method according to claim 8 comprising applying the said composition on bulbs or tubers by means of a coating device, wherein the device has a coating zone comprising:

a coating conveyor for conveying the bulbs or tubers in a longitudinal direction;

a device for applying a coating composition on the bulbs or tubers conveyed on the coating conveyor;

characterized in that the coating conveyor comprises a frame, a plurality of rotating brushes fixed in the longitudinal direction with respect to the frame, and a motor assembly to rotate the brushes about their respective axes transverse to the chassis, wherein the brushes are arranged in order to define together a surface for the supporting and conveying of the bulbs or tubers, and wherein the bulbs or tubers are rolled over during application of the coating composition.

10. Method according to claim 8 wherein it comprises the application of 0.2 to 1 kg of composition per tonne of bulbs and tubers.

11. Method according to claim 8 wherein it comprises the application on wet bulbs or tubers.

12. Composition according to claim 1 comprising 1 to 10% (weight/volume) of lecithin.

13. Composition according to claim 1 comprising 1 to 10% (weight/volume) of emulsifier or mixture of emulsifiers.

14. Anti-sprouting composition for application on wet bulbs and tubers consisting essentially of:

0.1 to 20% (weight/volume) of, 1 to 30% (weight/volume) of an emulsifier or mixture of emulsifiers selected from among anionic or non-ionic emulsifiers with a high hydrophilic/lipophilic balance (HLB), 10 to 80% (weight/volume) of a solvent selected from among water, monopropylene glycol, ethanol and mixtures thereof, wherein the composition comprises one more antioxidants selected from citric acid, clove oil and eugenol, and wherein the composition coats the wet bulbs and tubers.

15. Composition according to claim 14 comprising 1 to 10% (weight/volume) of lecithin.

16. Composition according to claim 14 comprising 1 to 10% (weight/volume) of emulsifier or mixture of emulsifiers.

17. Anti-sprouting composition for bulbs and tubers consisting of:
- 0.1 to 20% (weight/volume) of,
- 1 to 30% (weight/volume) of an emulsifier or mixture of emulsifiers selected from among anionic or non-ionic emulsifiers with a high hydrophilic/lipophilic balance (HLB),
- 10 to 80% (weight/volume) of a solvent selected from among water, monopropylene glycol, ethanol and mixtures thereof, wherein the composition comprises one more antioxidants selected from citric acid, clove oil and eugenol.

18. Composition according to claim 17 comprising 1 to 10% (weight/volume) of lecithin.

19. Composition according to claim 17 comprising 1 to 10% (weight/volume) of emulsifier or mixture of emulsifiers.

20. Composition according to claim 17 wherein the composition is for application on wet bulbs and tubers.

\* \* \* \* \*